United States Patent [19]

Flower

[11] Patent Number: 5,498,235
[45] Date of Patent: Mar. 12, 1996

[54] IONTOPHORESIS ASSEMBLY INCLUDING PATCH/CONTROLLER ATTACHMENT

[75] Inventor: Ronald J. Flower, Vernon, N.J.

[73] Assignee: Becton Dickinson and Company, Franklin Lakes, N.J.

[21] Appl. No.: 315,378

[22] Filed: Sep. 30, 1994

[51] Int. Cl.⁶ ............................................... A61N 1/30
[52] U.S. Cl. ........................... 604/20; 607/152; 439/909
[58] Field of Search ........................ 604/20–21; 607/152; 439/67, 909, 260, 495, 725, 267

[56] References Cited

U.S. PATENT DOCUMENTS

| | | |
|---|---|---|
| 4,522,211 | 6/1985 | Bare et al. ........................ 607/152 |
| 4,865,582 | 9/1989 | Sibalis . |
| 5,036,861 | 8/1991 | Sembrowich et al. . |
| 5,135,479 | 8/1992 | Sibalis et al. . |
| 5,403,275 | 4/1995 | Phipps ............................. 604/20 |

FOREIGN PATENT DOCUMENTS 652135B  6/1991  Australia ................................ 604/20

*Primary Examiner*—C. Fred Rosenbaum
*Assistant Examiner*—Mark Buckelman
*Attorney, Agent, or Firm*—Allen W. Wark

[57] ABSTRACT

An iontophoretic delivery system permits transcutaneous delivery of a drug contained on a patch. The system includes a flexible planar patch having a medicament-containing surface in contact with the skin of a patient. A controller supplies electrical current to the patch to effect iontophoretic delivery. Convenient removable attachment of the controller to the patch is provided so as to permit periodic drug administration.

11 Claims, 3 Drawing Sheets

IONTOPHORESIS ASSEMBLY INCLUDING PATCH/CONTROLLER ATTACHMENT

FIELD OF THE INVENTION

The present invention relates generally to an iontophoresis device for transcutaneous drug delivery. More particularly, the present invention relates to an iontophoretic assembly, including a drug-containing patch attachable to the skin and a controller which is connectable to the patch.

BACKGROUND OF THE INVENTION

Iontophoresis has come into increasing attention as an effective method for the application of drugs through the skin.

In practice, the process of iontophoretic drug delivery is typically achieved by placing an ionic drug either in solution or in gel form on a carrier and placing the drug-containing carrier into contact with the skin. A pair of electrodes is placed in contact with the skin and with the carrier. Direct current is applied between the two electrodes. Under the influence of the electric field present, drug molecules migrate through the skin. As current flows between the two electrodes placed at spaced apart locations on the skin, the current path carries the drug with it.

Delivery of a drug to the patient iontophoretically may be accomplished either at a constant rate over a long period of time, or periodically at various intervals and in some situations, upon demand. As can be seen, it may be necessary for the drug-containing carrier to be maintained in contact with the patient's skin over a long period of time, either for continuous drug delivery, or to permit frequent interval delivery over a period of time.

The iontophoretic delivery system may include a drug-containing carrier such as an adhesive patch and a controller having a source of electrical power and which is connectable to the patch for providing the necessary electrical current to deliver the drug. While effective devices are available for both providing a drug-containing patch for disposition on the skin of a patient and an electrical power source for applying iontophoretic effecting currents, oftentimes these devices remain connected to the patient even when iontophoretic delivery is not being effected.

In order to deliver a drug to the patch, the patch may be adhesively applied to the patient and the controller is attached to the patch. Oftentimes the controller is as large as, or larger than, the patch. It also should be somehow secured in place on the patient so that the patient may remain mobile and carry both the patch and controller with him as he moves about.

One of the problems with a transdermal drug delivery device such as described above, especially one that is compact and portable to provide patient mobility, is how to attach the controller to the patient and yet be as unobtrusive as possible and comfortable for the patient. A side-by-side arrangement of patch and controller may occupy too much space on the patient's skin and limit the choices where the transdermal device may be attached to the patient. Also, the controller may then have to be fastened to the patient's skin by adhesive or a strap, for example, which may be uncomfortable to the user.

Also, it is envisioned that the controller, which may contain sophisticated electronics besides just a power source to control and monitor the delivery of drug to the patient, is repeatedly used while the patch is discarded after use and replaced with new patches. The replaceable patches and controller should be so structured as to make it easy and convenient for the patient to replace used patches with new patches on the controller.

In situations where the periodic delivery of the drug is indicated, there is no need to maintain the source of electric current connected to the patch between doses. While the unobtrusive drug-containing patch may remain with the patient, removability of the current source would permit the patient to be free from cumbersome connection to the current source between doses. At such time as iontophoretic delivery of the drug is necessitated, the drug-containing patch attached to the patient's skin may be reconnected to the current source. However, to assure that the drug is administered properly, connections between current source and the patch must be reliably maintained.

It is therefore desirable to provide an interconnection assembly which permits the reliable interconnection between a drug-containing patch, positionable on the skin of a patient, and a source of electrical current for permitting iontophoretic delivery of the drug.

SUMMARY OF THE INVENTION

It is an object of the present invention to provide an improved iontophoretic drug delivery system for attachment to the skin of a patient for delivering a drug transcutaneously.

It is a further object of the present invention to provide an improved iontophoretic drug delivery system where the system includes a medicament-containing patch positionable on the skin of the patient and an electronic controller for controlling the iontophoretic delivery of the medicament through the skin.

It is still a further object of the present invention to provide a iontophoretic drug delivery system where the controller may be easily removably attached to the medicament-containing patch.

It is another object of the present invention to provide a drug delivery device which occupies minimal skin area on the patient and which is not cumbersome to the patient.

In the efficient attainment of these and other objects, the present invention provides a medicament containing disposable patch removably positionable on the skin of a patient in combination with a controller for electrically controlling the medicament delivery. A flexible planar patch body includes a medicament-containing first surface, an opposed second surface and an extending planar tab for insertable accommodation within the controller. The first surface of the planar patch body is supportable on the skin of the patient. The opposed second surface of the patch body is removably attached to the controller so as to secure the controller to the patch with the tab of the patch inserted into the controller.

As more particularly described by way of the preferred embodiment herein, the tab of the patch body may include an opening therethrough. The housing may include a post which receives the tab opening to secure the tab within the controller housing.

The tab of the patch is received in a slot formed in a sidewall of the controller housing. The flexible patch is then bent about its tab and secured to the top surface of the controller by Velcro mating hook and loop fasteners respectively mounted on the top surfaces of the controller housing and patch. In this way, the controller may be conveniently mounted on top of the patch, as the patch rests against the patient's skin. The bottom of the patch containing the drug to be delivered is exposed and may be adhesively secured to the patient's skin.

The controller housing may include electronics for providing a source of electrical current and the patch may include a pair of spaced electrodes electrically connected to the current source to permit iontophoretic delivery of the medicament contained thereon.

DETAILED DESCRIPTION OF THE PREFERRED EMBODIMENT

Figure 1:
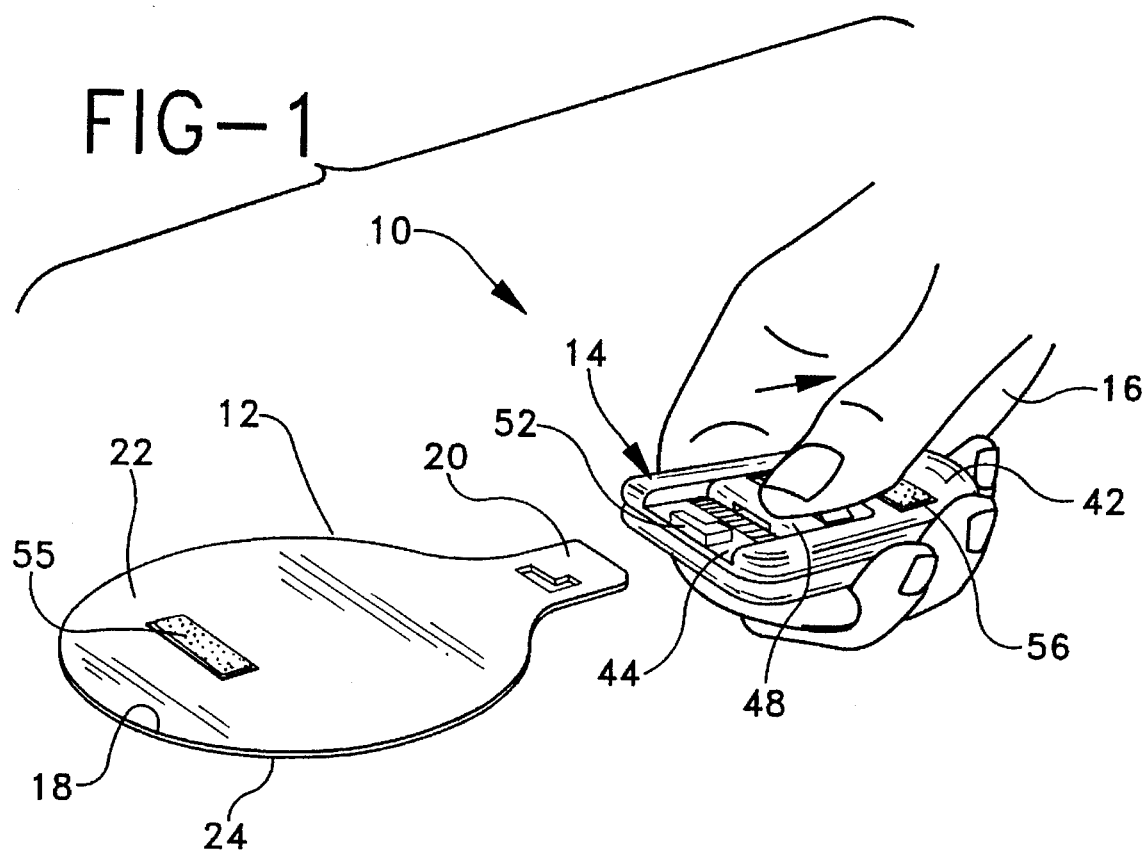
FIG. 1 is a perspective view of the combination of the patch and controller of the present invention in a disconnected condition.
Figure 2:
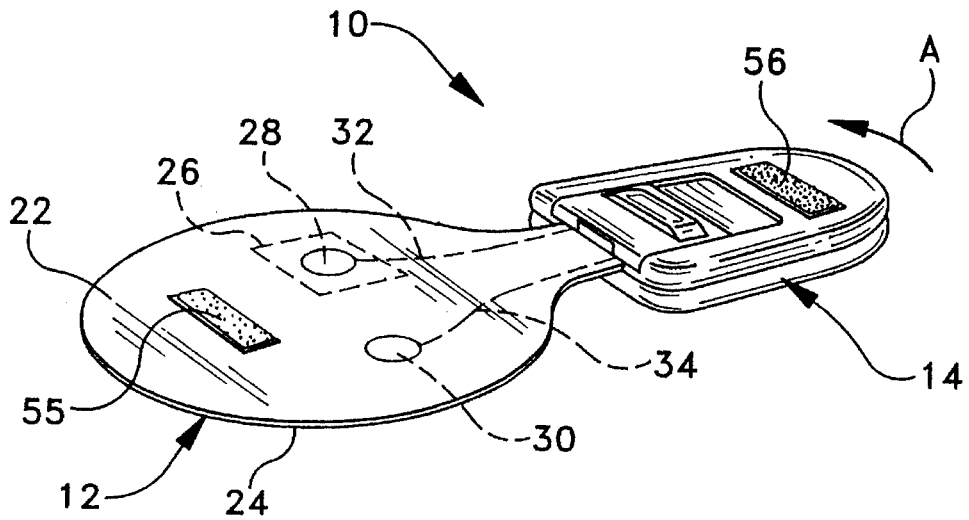
FIG. 2 is a perspective view of the patch and controller combination of the present invention shown in a connected condition.
Figure 6:
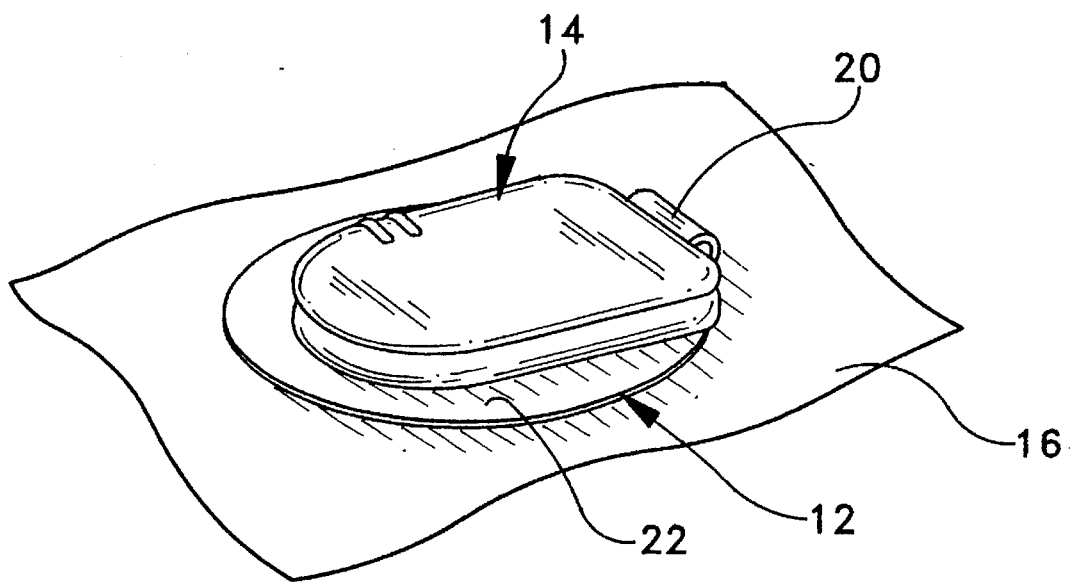
FIG. 6 is a perspective showing of the connected patch and controller of the present invention supported on the skin of a patient.

Referring to FIGS. 1 and 2, an iontophoretic patch and controller assembly 10 of the present invention is shown. Assembly 10 includes a patch 12 and a controller 14. Patch 12 is a generally planar flexible member formed of biocompatible material. Patch 12 may be formed of woven or non-woven textiles or polymers or may be any other construction well-known in the art. Patch 12 is adhesively supported on the skin 16 of the patient (FIG. 6). Patch 12 includes an enlarged patch body 18 and an extending narrow tab 20. Patch body 18 includes opposed planar surfaces 22 and 24. Planar surface 24 is disposed for skin contact and includes a drug reservoir 26 which contains an ionic drug typically in a gel form. While reservoir 26 is shown, any other technique known to place a drug in contact with the skin by use of a patch may also be employed. Skin contacting surface 24 further includes a pair of spaced apart electrodes 28 and 30. Each of electrodes 28 and 30 is positioned to be in contact with the skin upon placement of the patch 12 thereon. The positioning of electrodes 28 and 30 is such that an electrical current path is established between electrodes 28 and 30 through the skin of the patient. Electrode 28 is also placed in conductive contact with reservoir 26 in a manner well-known in the iontophoretic delivery art. A direct current source may be connected between the electrodes 28 and 30 such that electrode 28 in contact with reservoir 26 assumes the same charge as the ionized drug contained therein. Under the influence of electrical current passing from electrode 28 to electrode 30 through the skin, the drug contained in reservoir 26 is transcutaneously delivered.

Figure 3:
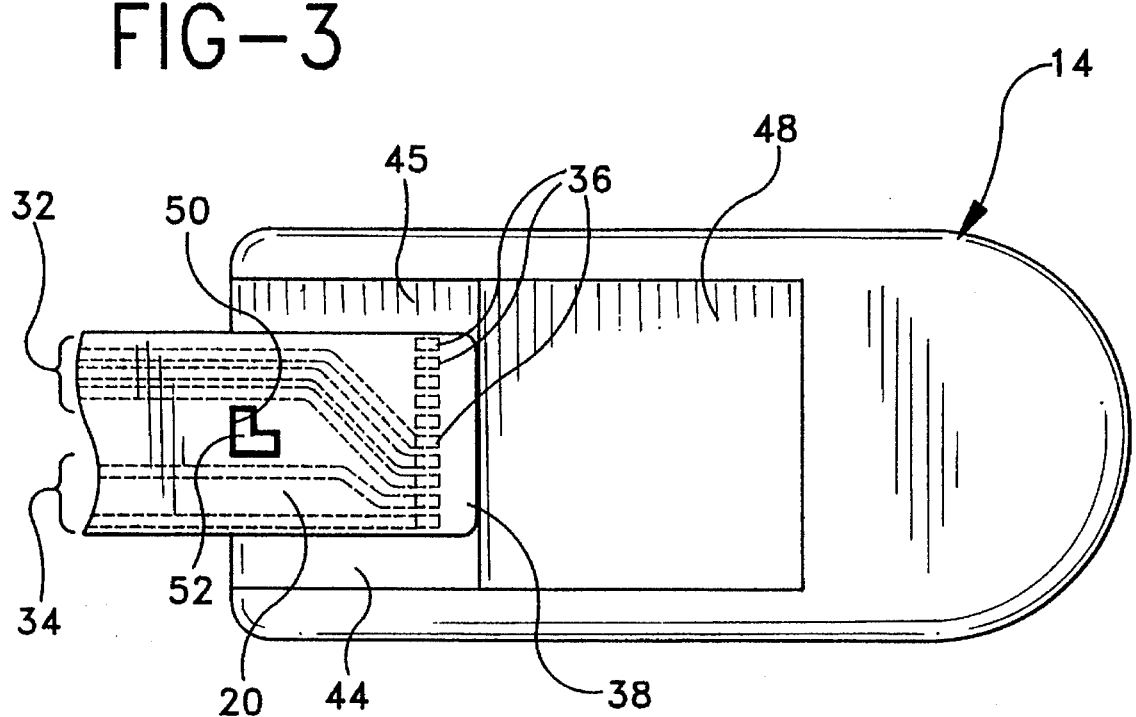
FIG. 3, the top plan view of a portion of the patch and the controller combination of FIG. 2.

As further shown in FIG. 3, electrical current is supplied to electrodes 28 and 30 via electrical traces 32 and 34. Each of traces 32 and 34 may be one or more conductive paths extending from electrodes 28 and 30 to exposed conductive pads 36 positioned adjacent a marginal edge 38 of tab 20. As will be described in further detail hereinbelow, pads 36 are positioned for electrical connection to the source of electrical current.

Figure 4:
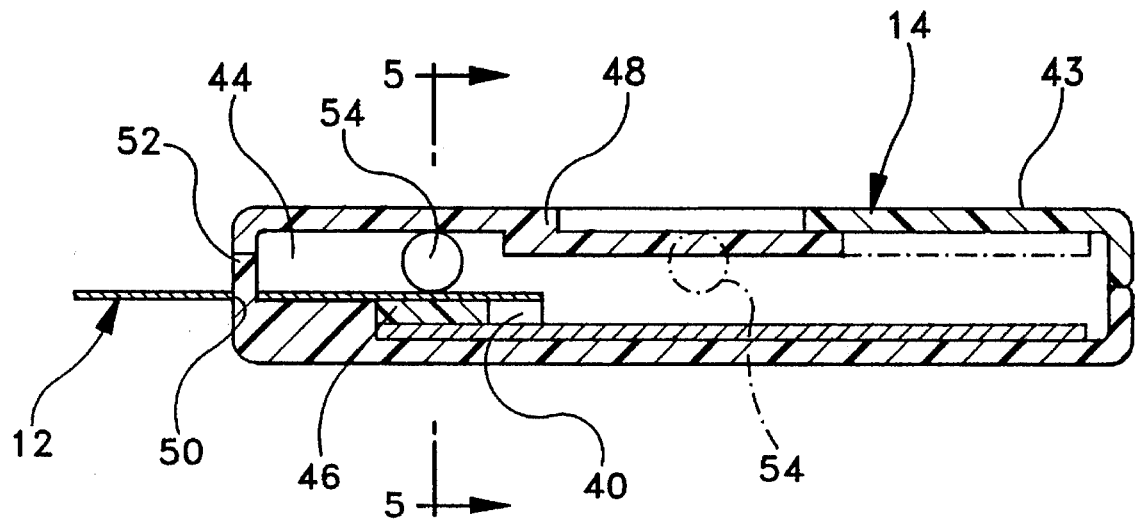
FIG. 4 is a vertical cross-sectional showing of the patch and controller combination of FIG. 3.
Figure 5:
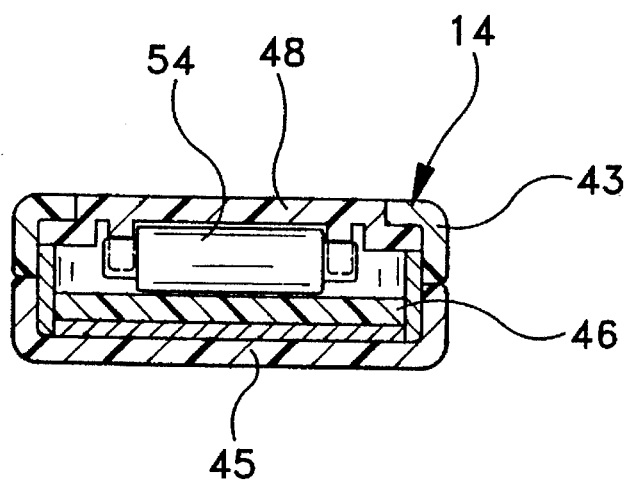
FIG. 5 is a horizontal cross-section of the combination of FIG. 4 taken through the lines 5—5 thereof.

Referring additionally to FIG. 4, controller 14 houses electronic components 40 which supply the controlled application of electric current to electrodes 28 and 30. As is known in the art, electrical components 40 may include a source of electrical power such as a battery (not shown) and additional electronic components used to send a controlled electrical current to electrodes 28 and 30.

Controller 14 includes a controller housing 42 which is generally rectangular in shape and includes an open front end 44 or a slot formed in the front end which accommodates or at least partially receives tab 20 of patch 12. Housing 42 further accommodates a connection array 46 adjacent electronic components 40. Connection array 46 may include plural electrical terminals in electrical connection with electronic components 40 and which are connectable to pads 36 of tab 20. In the present illustrative embodiment, connection array 46 is an electrical connection device known as a "zebra strip" having plural spaced-apart, exposed conductive surfaces 46a separated by insulation. It may be appreciated that any suitable electrical interconnection device may be employed in accordance with the present invention.

Housing 42 further includes a cover 48 which is used to close open front end 44 of housing 42. Cover 48 is slidably, captively retained on an upper wall 43 of housing 42. As shown in FIG. 1, cover 48 may be manually moved under thumb actuation to an open position exposing connection array 46 for electrical connection with pads 36 of tab 20. Cover 48 may be moved to a closed position shown in FIG. 2, covering connection array 46. With cover 48 in an open position patch 12 may be connected to controller 14.

In order to assure accurate alignment of pads 36 of tab 20 with the connection array 46 supported within housing 42, tab 20 is keyed to housing 42. Tab 20 includes an opening 50 which is designed to fit over an upwardly extending post 52. Opening 50 and post 52 are of similar shape so as to provide keyed accommodation of tab 20 and post 52. Post 52 extends upwardly from a bottom wall 45 of housing 42 adjacent the open front end 44 thereof. Post 52 is centrally located adjacent connection array 46 so as to accommodate tab 20 and positionally confine tab 20 within housing 44. The key structure included on both opening 50 and post 52 prevents incorrect positioning of patch 12 with respect to controller 14. In the present embodiment, both opening 50 and post 52 have a generally L-shaped cross section; however, any other mating shape which would prevent incorrect connection may be employed.

In order to assure intimate electrical engagement between pads 36 of tab 20 and the connection array 46, cover 48 carries a captively retained pressure roller 54 thereon. As shown in FIG. 4, the roller 54 is movable upon closure of cover 48 over tab 20 and connection array 46 to force pads 36 onto the conductive portions of connection array 46 establishing good electrical connection therebetween. The engagement of roller 54 also serves to secure patch 12 in connection with controller 14.

Referring again to FIG. 2, patch 12 and controller 14 include attachment means so as to permit the releasable support of controller 14 on patch 12 after interconnection between pads 36 and connection array 46 is established. Surface 22, which is opposed to skin-engaging surface 24 of patch 12 and the upper surface of housing wall 43 include cooperating fastening elements 55 and 56 thereon. In the present illustrative embodiment shown herein, the cooperative fastening elements include conventional hook and loop fasteners of the type sold under the trademark VELCRO. One cooperating fastening element 55 is secured adhesively or otherwise to patch 12 on surface 22 while the other cooperating fastening member 56 is secured by adhesive or otherwise to the upper surface of wall 43 of housing 42. As will be described in further detail hereinbelow, attachment of the mating hook and loop fasteners 55 and 56 provides for removable support of controller 14 on patch 12.

Having described the components of the patch and controller assembly 10 of the present invention, its operation may now be described.

Patch 12 may be adhesively secured to the skin 16 of the patient. Surface 24 of patch 12 is placed in intimate contact with the skin 16 so that electrodes 28 and 30 as well as drug-containing reservoir 26 are supported in good intimate contact with the skin 16. In order to effect iontophoretic delivery of the drug from reservoir 26 transcutaneously through skin 16, controller 14 is connected to patch 12. Cover 48 is retracted rearwardly under thumb actuation opening front end 44 of controller 14. Housing 42 is slipped over extending tab 20 of patch 12 so that opening 50 in tab 20 is seated over upwardly extending post 52 of housing 42. Proper planar orientation is assured between patch 12 and controller 14 due to the keyed matability between opening 50 and post 52. Cover 48 is then slid forwardly, closing cover 48 over tab 20. The captively retained roller 54 is rolled over tab 20 forcing electrical pads 36 of tab 20 into intimate electrical engagement with the conductive elements of connection array 46. Also, closure of cover 48 prevents removal of patch 12 from controller 14 as cover 48 overlies post 52. As controller 14 is designed to be left in electrical connection with patch 12 during iontophoretic delivery of the drug contained in reservoir 16, controller 14 may be fastened to patch 12 so that it will be conveniently retained on the skin of the patient. As shown in FIG. 2, once patch 12 is connected to controller 14, the controller may be flipped up in the direction of arrow A so that the mating hook and loop fasteners 55 and 56 engage each other to removably fasten controller 14 to patch 12 as shown in FIG. 6. The controller 14 is comfortably retained atop the patch on the skin of the patient during iontophoretic drug delivery. At such time as a particular application of the drug is completed, the controller may be removed by separating the mating hook and loop fasteners 55 and 56. Cover 40 may then be retracted, exposing post 52 permitting removal of tab 20 from controller 14. The controller may be then placed aside until the next administration of the drug is needed. The patch 12 may remain on the skin of the patient, eliminating the need for frequent replacement of the patch.

The drug delivery device of the present invention is comfortable for the patient to wear and occupies very little space on the patient's skin. The flexibility of the patch and the flip-up design of the drug delivery device allows the controller to be secured to the unused top surface of the patch and to be directly positioned over the patch. Of course, the drug delivery device may still operate with the patch and controller interconnected and positioned side-by-side if the user so desires, such as with short-term treatments, for example.

The tab of the patch is secured in place to the controller when the lid is closed and properly aligned by the keyed post in the controller to ensure that the electrical connection between the patch and the controller is correct.

Various changes to the foregoing described and shown structures would now be evident to those skilled in the art. Accordingly, the particularly disclosed scope of the invention is set forth in the following claims.

What is claimed:

1. In combination:

a medicament-containing disposable patch removably positionable on the skin of a patient for permitting iontophoretic delivery of medicament transcutaneously; and a controller including electronic components for electrically controlling said medicament delivery;

the patch including a flexible planar patch body having a medicament-containing first surface, an opposed second surface and an extending planar tab for insertable electrical accommodation in said controller, said first surface of said planar patch body being supportable on the skin of said patient;

said opposed second surface of said patch body and said controller including co-operative removable fastening means for removably fastening said controller to said patch and for maintaining said controller in a fastened condition with respect to said patch with said tab electrically accommodated in said controller.

2. A combination of claim 1 wherein said controller includes a controller housing supporting said electronic components therein and wherein said housing includes a housing opening for receipt of said patch body tab.

3. A combination of claim 2 wherein said patch body includes a pair of spaced apart electrodes one of said electrodes being positioned for contact with said medicament on said first surface and the other electrode positioned for contact with the skin of the patient and wherein said tab includes electrical connection pads in electrical engagement with said electrodes.

4. A combination of claim 3 wherein said electronic components supported in said controller housing include electrical connection elements supported adjacent said housing opening and engagable with said electrical connection pads for establishing electrical connection between said electronic components of said controller and said electrodes of said patch body.

5. A combination of claim 2 wherein said controller housing includes a first housing surface and an opposed second housing surface and wherein upon insertion of said tab into said housing, said first housing surface is generally aligned with the second surface of planar patch body.

6. A combination of claim 5 wherein said co-operative removable fastening means includes a first fastening element supported on said first surface of said housing and a second fastening element supported on said second surface of said planar body;

said first and second fastening elements being securable to each other upon placement of said first housing surface in contact with said second surface of said planar patch body.

7. A combination of claim 6 wherein each said tab and said housing include co-operating locking means for removably securing said tab in said housing opening.

8. A combination of claim 6 wherein said housing includes a housing post extending adjacent said housing opening and wherein said tab includes a tab opening for insertably accommodating said post therein upon insertion of tab in said housing.

9. A combination of claim 8 wherein said housing includes a movable cover, said cover being movable between an open position exposing said post for removable accommodation of said tab, and a closed position preventing removal of said tab from said post.

10. A combination of claim 9 further including means activatable upon movement of the cover from said open position to said closed position for securing said tab over said post.

11. A combination of claim 9 wherein said activatable means include a roller for movement over said tab supported over said post.

* * * * *